United States Patent
Lin

(10) Patent No.: US 8,361,403 B2
(45) Date of Patent: Jan. 29, 2013

(54) ULTRASONIC OZONE-GENERATING UNIT

(75) Inventor: Chin-Yuag Lin, Taiping (TW)

(73) Assignees: America Fuji Healthware, Inc., Monterey Park, CA (US); Philip Huang, Monterey Park, CA (US)

(*) Notice: Subject to any disclaimer, the term of this patent is extended or adjusted under 35 U.S.C. 154(b) by 330 days.

(21) Appl. No.: 12/770,657

(22) Filed: Apr. 29, 2010

(65) Prior Publication Data

US 2011/0268620 A1 Nov. 3, 2011

(51) Int. Cl.
*B01J 19/08* (2006.01)
(52) U.S. Cl. ............ 422/186.07; 422/186; 422/186.18; 204/176; 68/183; 134/102.1; 134/102.2; 134/57 D; 134/58 D
(58) Field of Classification Search ............. 422/186.07, 422/186, 186.18; 204/176; 68/183; 134/102.1, 134/102.2, 57 D, 58 D
See application file for complete search history.

(56) References Cited

U.S. PATENT DOCUMENTS 6,363,951 B1 * 4/2002 Wood .................... 134/102.2

\* cited by examiner

*Primary Examiner* — Xiuyu Tai
(74) *Attorney, Agent, or Firm* — Hershkovitz & Associates, LLC; Abraham Hershkovitz

(57) ABSTRACT

The ultrasonic ozone-generating unit in accordance with the present invention has an ozone-generating device, an independent seat, a sink device, an utensil-holding device and a vegetable basket. The utensil-holding device and the vegetable basket are mounted in a receiving space of the independent seat or in a sink of the sink device. An ozone gas generated by the ozone-generating device with a close-type air-pumping device capable of producing powerful ultrasonic carrier-airflow is guided into the receiving space or the sink and dissolved in water to sterilize deodorize and bleach an object to be cleansed.

1 Claim, 8 Drawing Sheets

ULTRASONIC OZONE-GENERATING UNIT

BACKGROUND OF THE INVENTION

1. Field of the Invention

The present invention relates to an ultrasonic ozone-generating device, especially to an ultrasonic ozone-generating unit and an appliance comprising the ultrasonic ozone-generating which generates a powerful ultrasonic carrier-airflow. With the ultrasonic ozone-generating device and an appliance comprising the ultrasonic ozone-generating, an ozone gas of great volume generated by an ozone generator with a close-type air-pumping device is guided into a receiving space of an independent seat or into a sink of a sink device. The ozone gas is dissolved in water for sterilizing, deodorizing and bleaching objects to be cleansed.

2. Description of the Prior Art

Rapidly developing human society continuously consumes environmental resources and greatly pollutes the environment in which we live. For instance, air-pollution, waste disposal problems, water-pollution and food-pollution are hazardous to goods indispensable to human basic needs. In other words, humans suffer from their own success. Other than environmental education, cleansing machines are researched and developed to address the environmental issues. Such cleansing machines eliminate pollutants from food, drinking water and air and thus protect humans from hazardous materials. The research and development of such cleansing machine are considered an important issue in relevant fields as well as to society in general.

Hence, a manufacturer provided a conventional single-functional ozone-generating machine which can be hung or placed beside a kitchen sink for cleansing water or vegetable. However, the applicable range of the machine is significantly insufficient due to lack of ozone gas transportability for sterilizing, deodorizing and bleaching a large amount of objects to be cleansed. It is noted that the conventional machine is incapable of rapidly sterilizing/detoxifying food in everyday life.

To overcome the shortcomings, the present invention provides an ultrasonic ozone-generating unit to mitigate or obviate the aforementioned problems.

SUMMARY OF THE INVENTION

The main objective of the invention is to provide an ultrasonic ozone-generating unit.

The ultrasonic ozone-generating unit in accordance with the present invention has an ozone-generating device, an independent seat, a sink device, a utensil-holding device and a vegetable basket. The utensil-holding device and the vegetable basket are mounted in a receiving space of the independent seat or in a sink of the sink device. An ozone gas generated by the ozone-generating device with a close-type air-pumping device capable of producing powerful ultrasonic carrier-airflow is guided into the receiving space or the sink and dissolved in water to sterilize deodorize and bleach an object to be cleansed.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
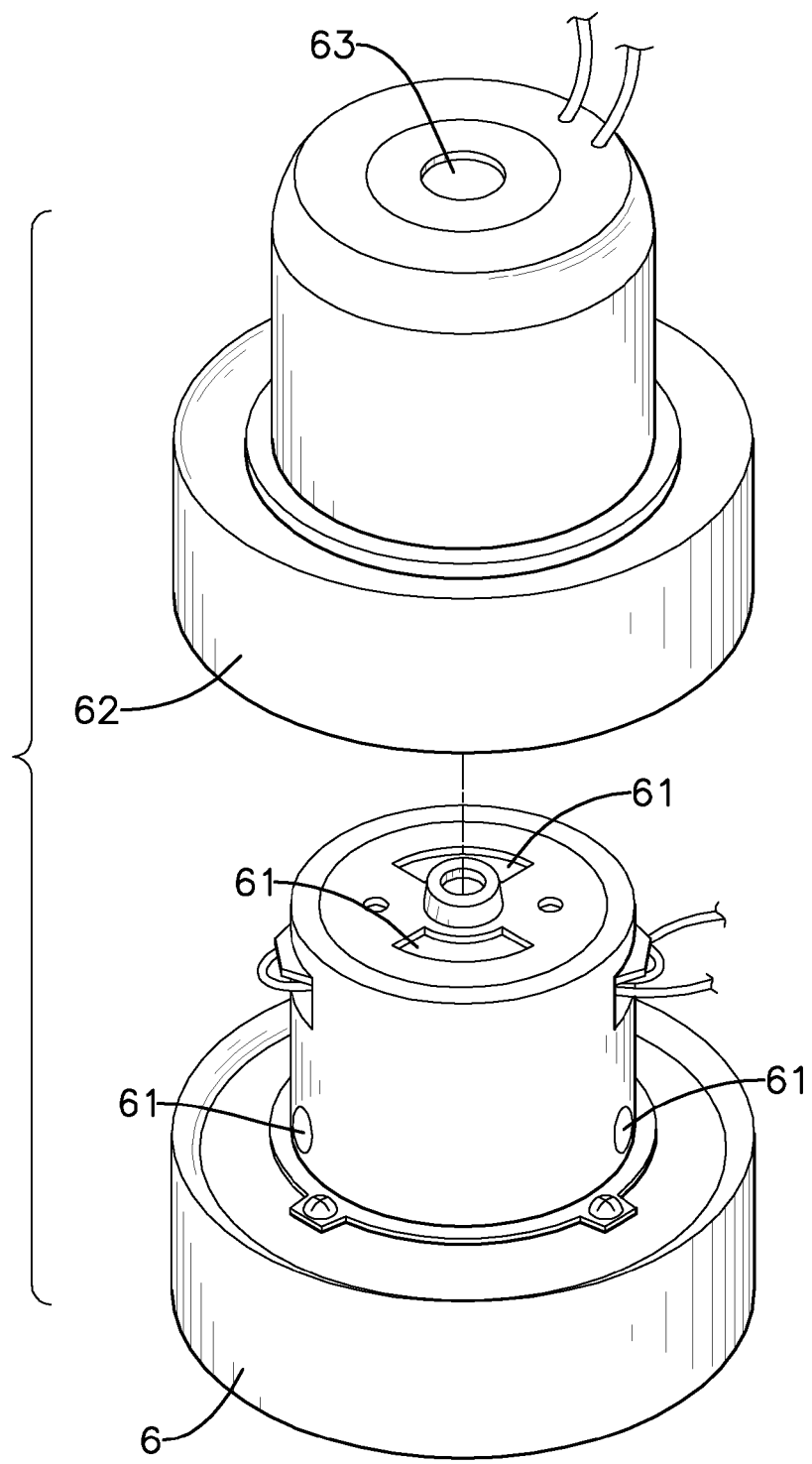
FIG. 1 is an exploded perspective view of an air pump of an ultrasonic ozone-generating unit in accordance with the present invention.
Figure 2:
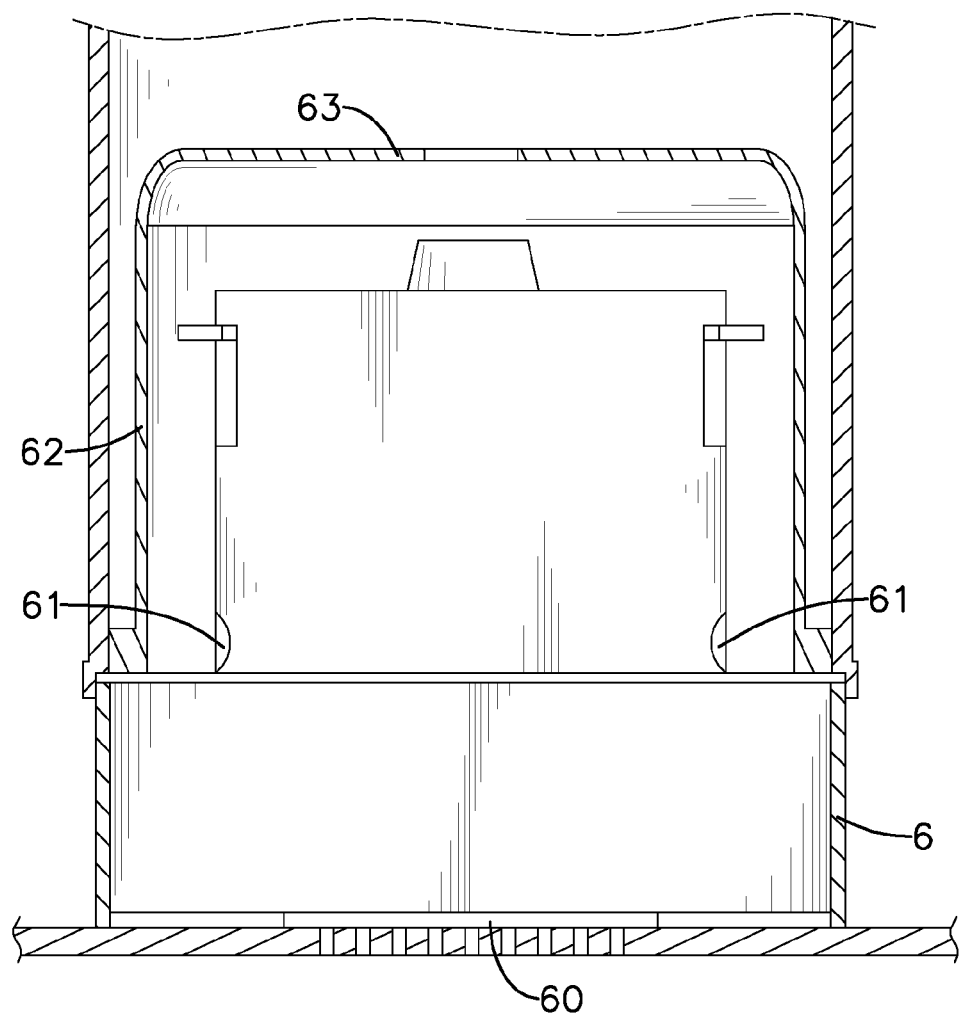
FIG. 2 is a cross-sectional side view of the air pump of the ultrasonic ozone-generating unit in FIG. 1.
Figure 3:
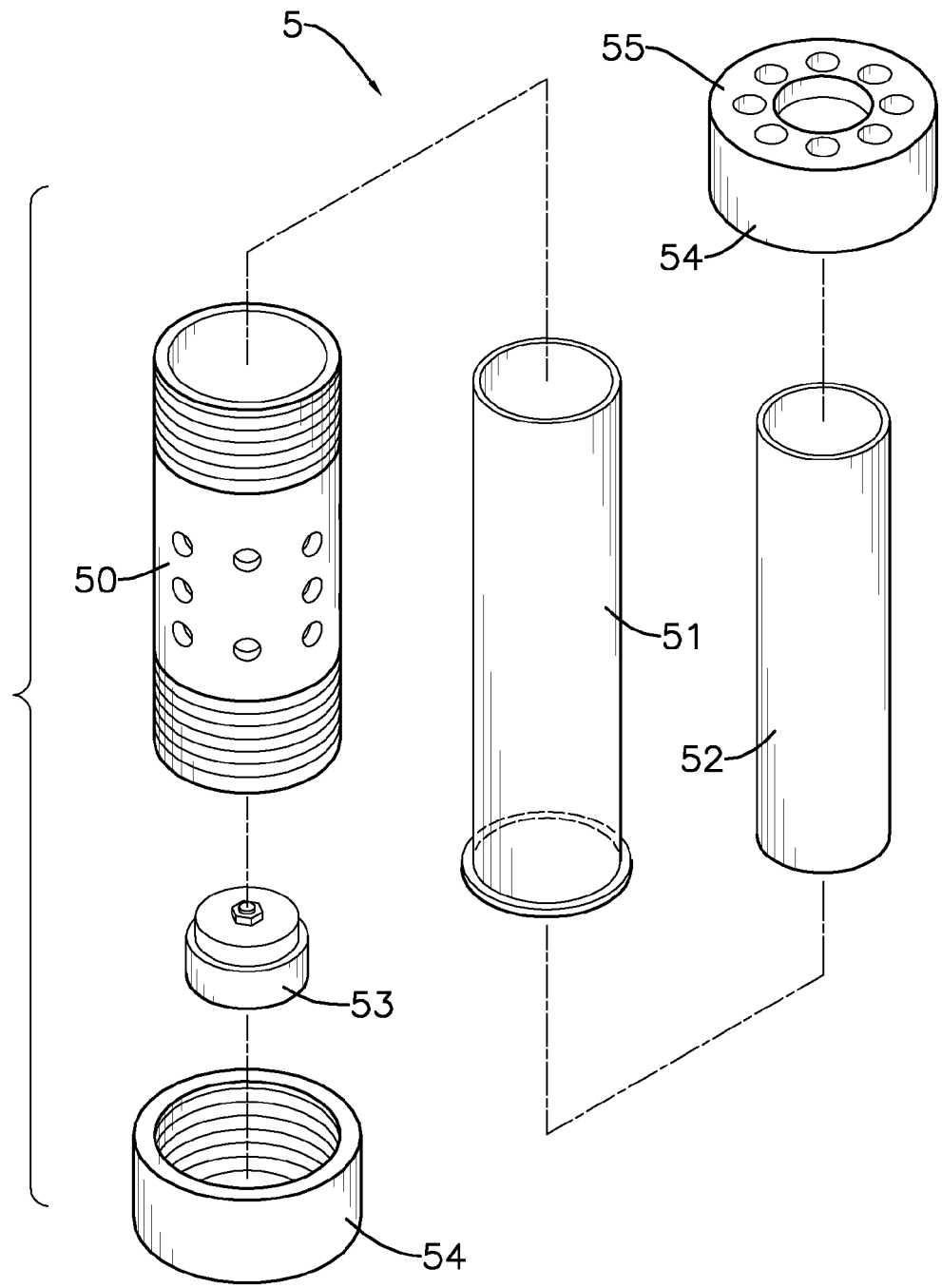
FIG. 3 is an exploded perspective view of an ozone generator of the ultrasonic ozone-generating unit in FIG. 1.
Figure 4:
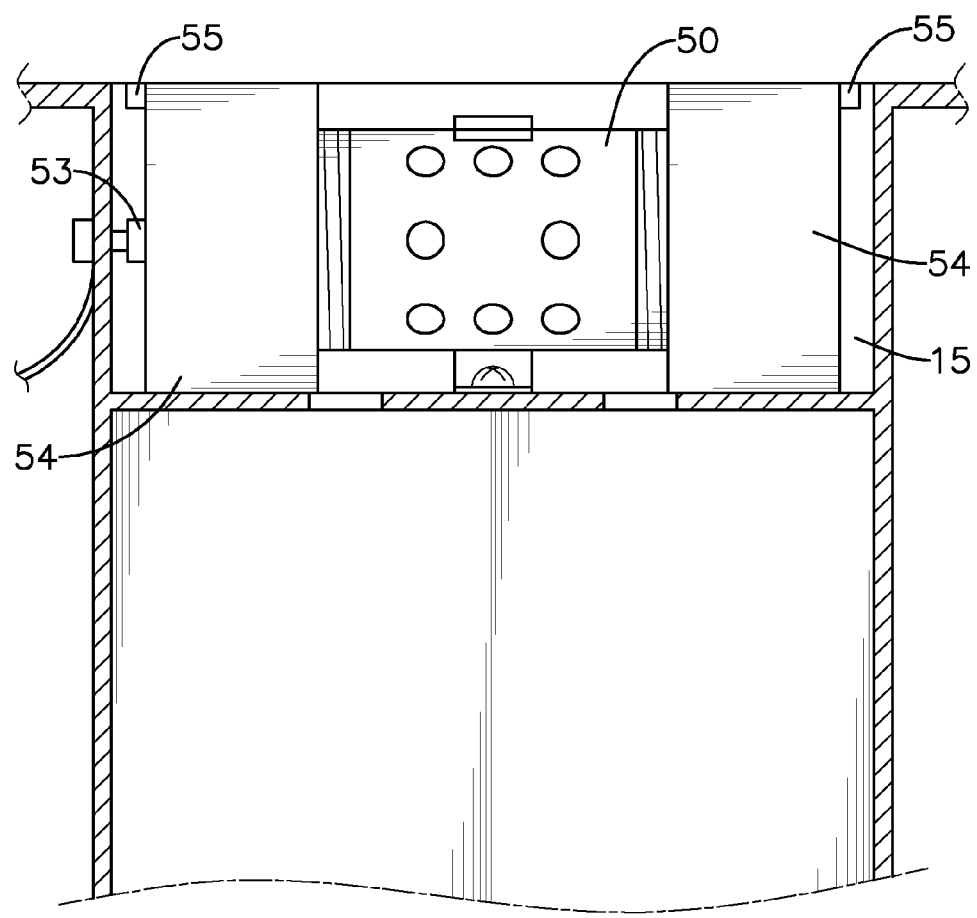
FIG. 4 is a cross-sectional side view of the ozone generator in FIG. 3.
Figure 5:
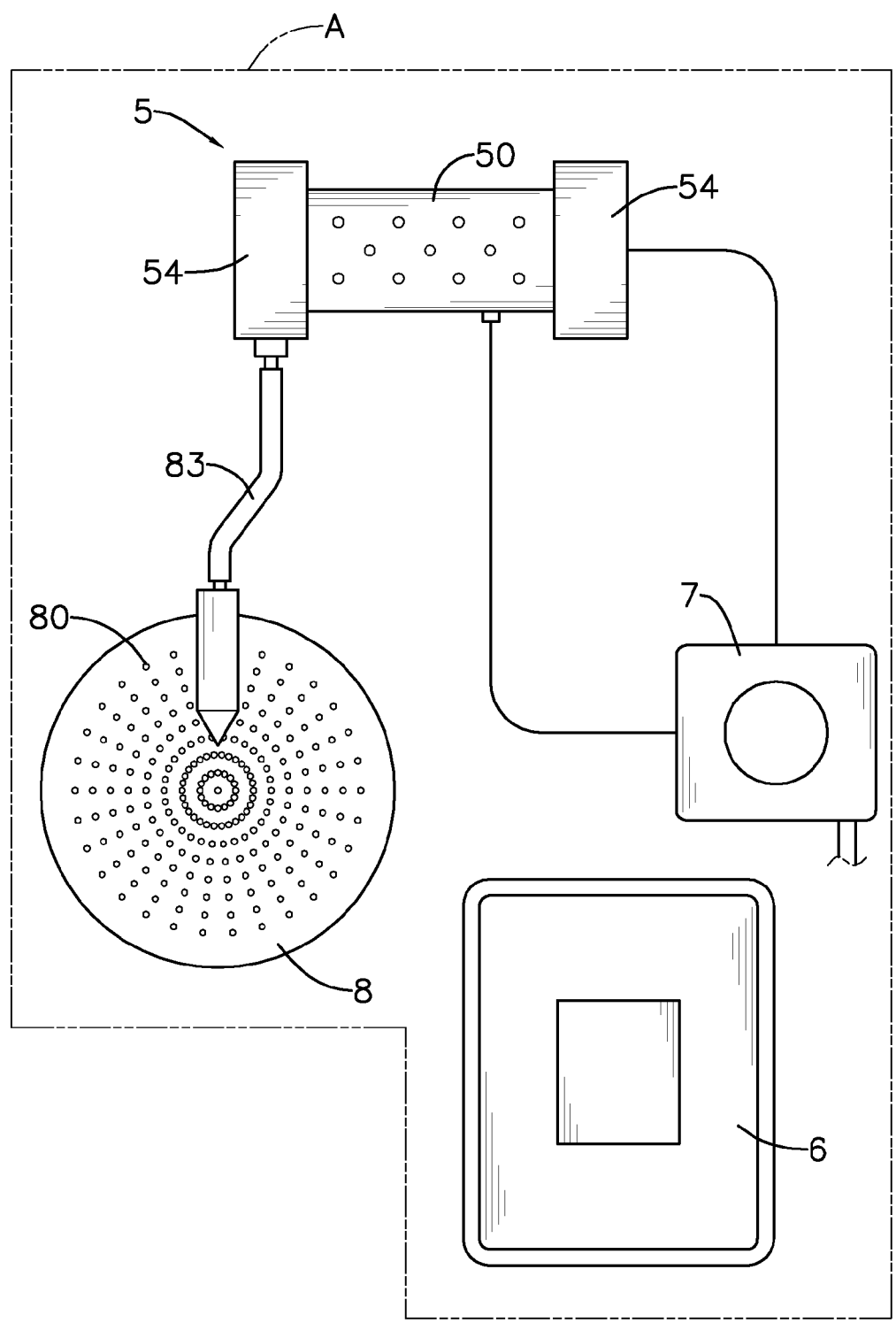
FIG. 5 is a schematic diagram of an ozone-generating device of the ultrasonic ozone-generating unit in FIG. 1.
Figure 6:
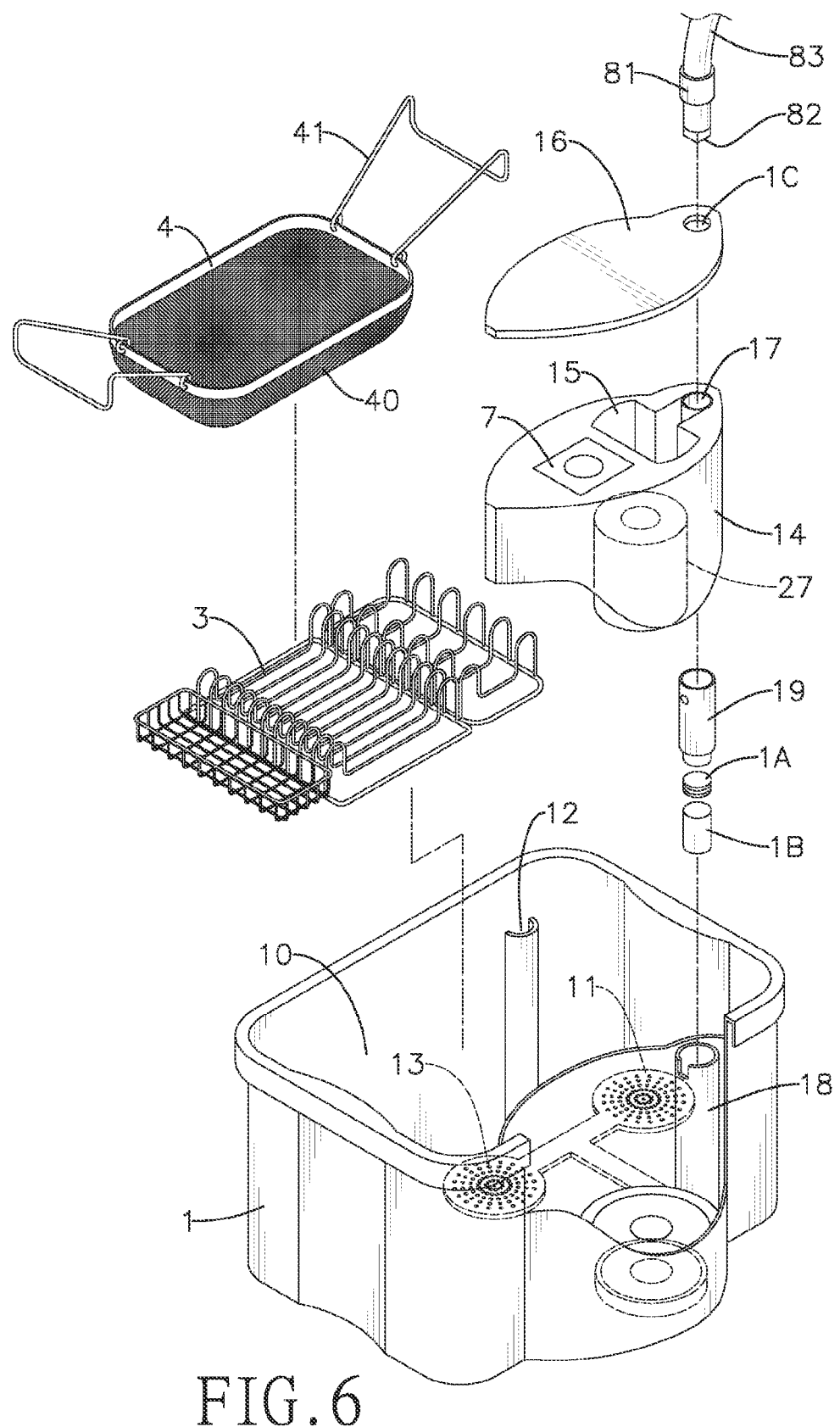
FIG. 6 is an exploded perspective view of the ultrasonic ozone-generating unit in FIG. 1 with an independent seat.
Figure 7:
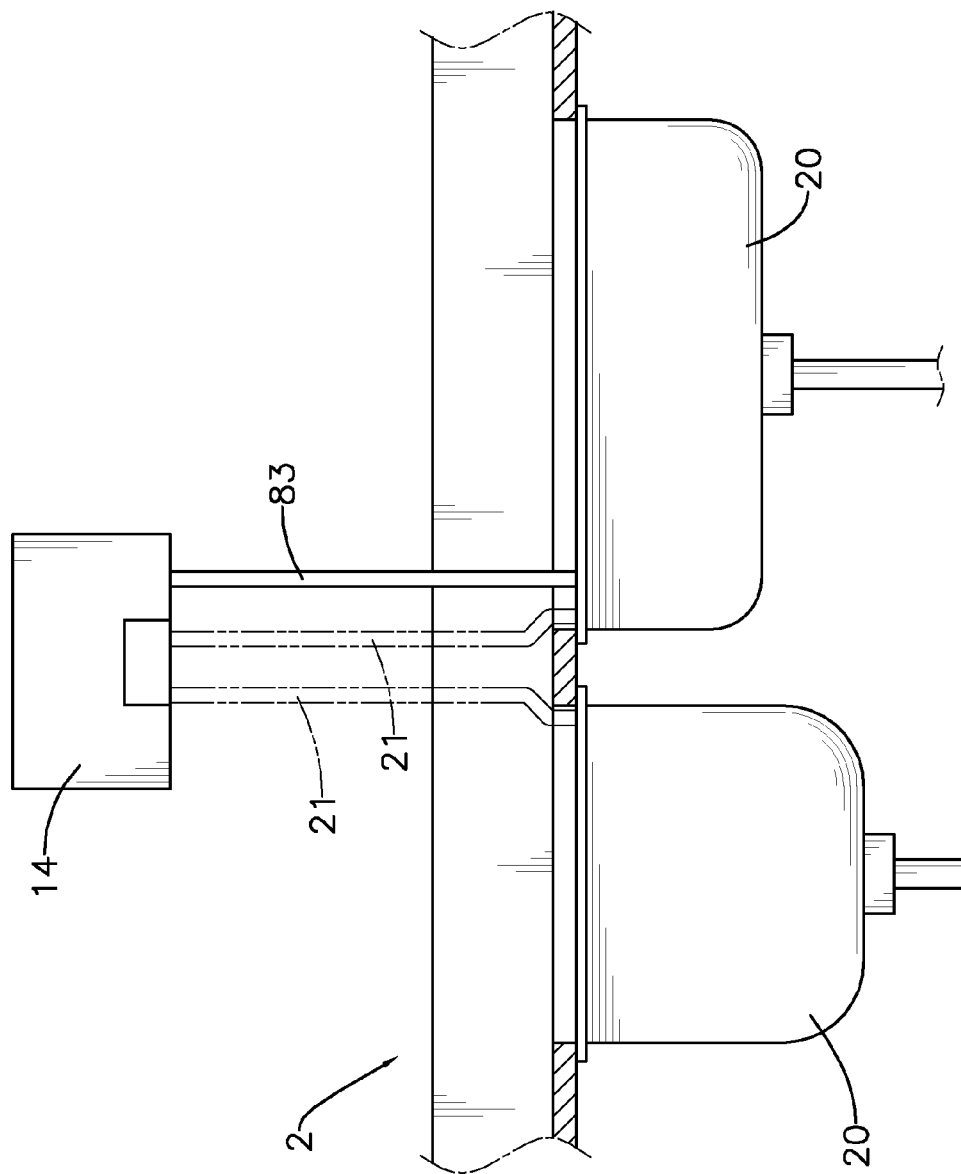
FIG. 7 is a cross-sectional front view of the ultrasonic ozone-generating unit in FIG. 1 with a sink device.
Figure 8:
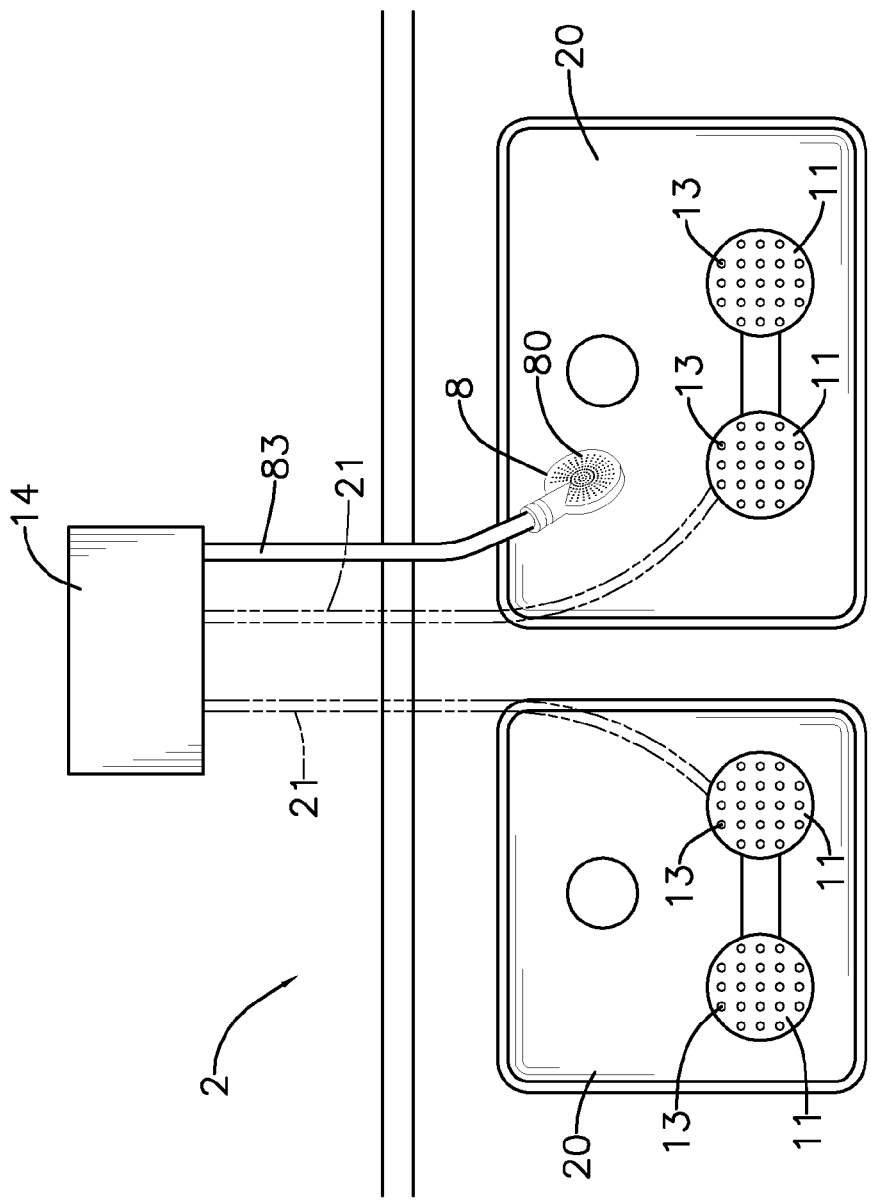
FIG. 8 is a top view of the ultrasonic ozone-generating unit in FIG. 7.

With reference to FIGS. 1-8, an ultrasonic ozone-generating unit in accordance with the present invention comprises an ozone-generating device (A), an independent seat (1), a sink device (2), a utensil-holding device (3) and a vegetable basket (4).

The ozone generator (A) is used for generating ozone by connecting with a high voltage generator (7). The ozone generating device (A) comprises an ozone generator (5) and an air pump (6). The ozone generator (5) comprises a cathode screw pipe (50), an anode glass tube (51), an excitation device (52), a pair of screwing cap rings (54), an anode connector head (53) and two handles (55).

The cathode screw pipe (50) comprises two ends.

The anode glass tube (51) is mounted in the cathode screw pipe (50).

The excitation device (52) is mounted in the anode glass tube (51).

The screwing cap rings (54) are screwed in both ends of the cathode screw pipe (50). Each screwing cap ring (54) comprises an end surface.

The anode connector head (53) is for inserting into any of the screwing cap rings (54).

The two handles (55) are for applying a force for easy removal of the ozone generator. The two handles (55) are respectively attached to the end surfaces of the two screwing cap rings (54).

The air pump (6) is mounted in the ozone generator and used as an ultra-high-speed-gas-emitting device. The air pump (6) a lower end, an air inlet (60) formed on the lower end, an upper end, a side edge, multiple air outlets (61) and a rubber seal cap (62).

The air inlet (60) is formed on the lower end of the air pump (6).

The multiple air outlets (61) are formed on the upper end and the side edge of the air pump (6).

The rubber seal cap (62) is mounted to the upper end of the air pump (6) and comprises a nozzle (63). The rubber seal cap (62) may raise a gas pressure in the rubber seal cap (62) by collecting air. The collected air is then forced out from the nozzle (63) toward the ozone generator (5) to generate an ultrasonic airflow.

The independent seat (1) comprises a body, two side edges, a lead pipe and a control box (14), as well as a fore end, a sleeve (18), a receiving space (10), a gas-guiding disc (11) and an overflow port (12).

The receiving space (10) is downward recessed in the independent seat (1). The receiving space may receive a fluid or an object to be cleansed.

The gas-guiding disc (11) is formed in the receiving space (10) and comprises multiple outlet holes (13).

The overflow port (12) is formed in the receiving space (10).

The lead pipe is connected to the ozone generator (5).

The control box (14) is attached to the fore end of the body of the independent seat (1) and comprises a body, a high-voltage generator (7), an ozone-transporting pipe (17), an upper surface, a cover plate (16), a fore end surface, a switch (27), a mounting hole (1C), a bubble-outputting disc (8) and a sleeve-head-connecting pipe (81) and an ozone-retaining chamber (15).

The high-voltage generator (7) is attached to the control box (14).

The ozone-transporting pipe (17) is inserted into the sleeve (18) of the independent seat (1) and comprises an ozone sleeve head (19), a stopper (1A) and a resilient device (1B). The stopper (1A) and the resilient device (1B) are combined with the ozone sleeve head (19).

The cover plate (16) seals the upper surface of the control box (14) and comprises a mounting hole (1C). The mounting hole (1C) corresponds with the ozone-transporting pipe (17).

The switch is attached to the fore end surface of the control box (14) for switching power supply or for adjusting bubble level.

The bubble-outputting disc (8) comprises multiple bubble-outputting holes (80).

The sleeve-head-connecting pipe (81) is inserted in one of the bubble-outputting holes (80) and is connected to the bubble-outputting disc (8). The sleeve-head-connecting pipe (81) comprises a leading pipe (83), an end and multiple radial holes.

The leading pipe (83) is connected to the bubble-outputting disc (8). With the leading pipe (83), the sleeve-head-connecting pipe (81) is connected to the bubble-outputting disc (8).

The radial holes (82) are formed on the end of the sleeve-head-connecting pipe (81).

The sink device (2) comprises a surface, at least one sink (20) and at least one gas-guiding disc (11).

The at least one sink (20) if formed on the surface of of the sink device (2).

The at least one gas-guiding disc (11) is formed in the at least one sink (20) and is connected to the ozone generator (5) that is connected to the control box (14). The at least one gas-guiding disc (11) is for guiding an ozone gas generated by the ozone generator (5) into the at least one sink (20) to sterilize, deodorize and bleach an object to be cleansed. The at least one gas-guiding disc (11) comprises multiple outlet holes (13). The ozone gas generated by the ozone generator (5) is guided through the multiple outlet holes (13) into the sink.

The utensil-holding device (3) may be mounted in the receiving space

The utensil-holding device (3) may be mounted in the receiving space (10) of the independent seat (1) for holding utensils such as bowls, plates and/or chopsticks.

The vegetable basket (4) is mounted in the receiving space (10) of the independent seat (1) and comprises two ends, a net (40) and a holder hook (41). The net (40) is mounted over the two side edges of the independent seat (1) and hung into the receiving space (10) of the independent seat (1). The sterilizing, deodorizing and bleaching function may be performed on an object to be cleansed held in the net (40). The net (40) comprises two ends. The holder hook (41) is pivotally mounted to the two ends of the net (40). The holder hook (41) mounts the net (40) over the two side edges of the independent seat (1) allowing the net to be hung into the receiving space (10) of the independent seat (1).

When using the ultrasonic ozone-generating unit in accordance with the present invention comprising the aforementioned structure, the user pours water into the receiving space (10) of the independent seat (1) and starts the ozone-generating device (A) to generate ozone with the ozone generator (5). At the same time the user starts the air pump (6) which synchronously operates at ultra high spinning speed to generate powerful ultrasonic airflow. The ozone flows through the gas-guiding disc (11) into the receiving space (10) and is dissolved in water, which further provides wider application of the ultrasonic ozone-generating unit in accordance with the present invention other than aforementioned sterilizing, deodorizing and bleaching functions.

The ultrasonic ozone-generating unit in accordance with the present invention is capable of following applications.

1. The ultrasonic ozone-generating unit in accordance with the present invention is capable of sterilizing, detoxifying, removing fishy smell from and preserving vegetables, fruits, seafood and meat. In other words, the ultrasonic ozone-generating unit in accordance with the present invention helps cleanse the surfaces of vegetables, fruits, seafood and meat and prevent them from rotting due to their tendency to be oxidized. Furthermore, the ultrasonic ozone-generating unit protects vegetables and fruits from residual agricultural chemicals and parasite eggs, we well as seafood and meat from unpleasant odor.

2. The ultrasonic ozone-generating unit in accordance with the present invention is capable of sterilizing and detoxifying in a chamber, a room, a hotel, a restaurant or a hospital. The ultrasonic ozone-generating unit is also capable of eliminating smoke, dust, fungi, and bacteria from a room as well as degrading hazardous substances. As a result of the work of the ultrasonic ozone-generating unit, the air in a room will become clean and fresh and have a refreshing fragrance. It is known that clean and fresh air is vital to protect infants and children from infectious diseases. Deodorizing and dust eliminating with the ultrasonic ozone-generating unit after house cleaning demonstrate most immediate and significant effect. The ultrasonic ozone-generating unit is also effective for deodorizing a room or a wardrobe, eliminating in-door-refluxing smoke and preventing fungi growth.

3. The ultrasonic ozone-generating unit in accordance with the present invention is also capable of sterilizing and deodorizing within an icebox to improve the preservation capability of the icebox, eliminate unpleasant odor from food such as seafood and meat and prevent the unpleasant odor from spreading. The effects of the aforementioned functions are immediate and significant.

4. The ultrasonic ozone-generating unit is also capable of deodorizing within a toilet, a bathroom or a kitchen. The ammonical odor in a toilet, the greasy fumes and the fishy smell in a kitchen and the odor of a pesticide may all be mitigated or deodorized with the ultrasonic ozone-generating unit.

5. The ultrasonic ozone-generating unit may be used to sterilize and cleanse tools and clothes. Tools, utensils, scrubbing cloth and clothes may not be completely cleaned in ordinary cleansing procedures or residual detergents may remain therewithin. The ultrasonic ozone-generating unit not only provides enhanced sterilizing and cleansing functions but also compensates the ordinary cleansing procedures by oxidation of the residual detergents.

6. The ultrasonic ozone-generating unit may also be used for skin whitening and skin cleansing. Toxins in unclean water may be easily passed into skin and induce skin aging and melanin precipitation. Washing or bathing with clean water in which ozone is dissolved not only stops skin aging and prevents melanin precipitation but also effectively cleans the face of the user and improve the status of the skin. That is, the ultrasonic ozone-generating unit is capable of improving the status of the skin by inhibiting bacterial infection and formation of acne, pigmented spot and senile plaque.

7. The ultrasonic ozone-generating unit is capable of eliminating bacteria from and deodorizing pets and trash. The ultrasonic ozone-generating unit provides ozone for eliminating bacteria from the body of a pet and deodorizing the excrements, which can be extremely disturbing. Trash accumulated in a waste dump generates disturbing odor and allows pests such as mosquitoes or cockroaches to grow. The ultrasonic ozone-generating unit may be used to deodorize the trash and inhibit the growth of the insects.

8. The ultrasonic ozone-generating unit in accordance with the present invention is also capable of deodorizing and killing fungi within a wardrobe or a shoebox. Sneakers, boots and socks may be sterilized with ozone with the ultrasonic ozone-generating unit before and after use to prevent athlete's foot and embarrassing odor. Especially during a period of seasonal transition, the user may easily observe significant growth of fungi on clothes stored in a wardrobe and a musty odor in leather wears. With the ultrasonic ozone-generating unit, the user will be able to easily solve the aforementioned problems.

9. The ultrasonic ozone-generating unit may also used to refresh, sterilize and deodorize water in a fish-breeding tank, which promotes the health of fish. In addition, ozone is helpful for deodorizing fish and enhancing the color of the fish.

By sealing the air pump (6) with the rubber seal cap (62), the powerful airflow generated by the hyper spinning air pump (6) concentrates and rapid and effectively outputs the ozone generated by the ozone generator (5) that concentrates supersonic energy. With the ultrasonic ozone-generating unit, humans can enjoy the deodorizing, sterilizing and bleaching functions of ozone in a more inventive way than ordinary similar products current available in market.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An ultrasonic ozone-generating unit comprising
    an ozone-generating device comprising
        an ozone generator used for generating ozone by connecting with a high voltage generator and comprising
            a cathode screw pipe comprising
                two ends;
            an anode glass tube mounted in the cathode screw pipe;
            an excitation device mounted in the anode glass tube;
            a pair of screwing cap rings screwed in both ends of the cathode screw pipe and each comprising
                an end surface;
                an anode connector head for inserting into the screwing cap ring; and
                two handles for applying a force for easy removing of the ozone generator and respectively attached to the end surfaces of the two screwing cap rings; and
    an air pump mounted in the ozone generator, used as an ultra-high-speed-gas-emitting device and comprising
        a lower end;
        an air inlet formed on the lower end;
        an upper end;
        a side edge;
        multiple air outlets formed on the upper end and the side edge; and
        a rubber seal cap mounted to the upper end for raising a gas pressure therein by collecting air before flowing the collected air out toward the ozone generator to generate an ultrasonic airflow and comprising
            a nozzle from which the collected air are flown out toward the ozone generator;
    an independent seat comprising
        a fore end;
        a sleeve;
        a receiving space downward recessed for receiving a fluid or an object to be cleansed;
        a gas-guiding disc formed in the receiving space and comprising
            multiple outlet holes formed on the gas-guiding disc; and;
        an overflow port formed in the receiving space;
    a lead pipe connected to the ozone generator; and
    a control box attached to the fore end of the independent seat and comprising
        an ozone-retaining chamber;
        the high-voltage generator;
        an ozone-transporting pipe inserted into the sleeve of independent seat and comprising
            an ozone sleeve head;
            a stopper combined with the ozone sleeve head; and
            a resilient device combined with the ozone sleeve head;
        an upper surface;
        a cover plate sealing the upper surface and comprising
            a mounting hole formed in the cover plate and corresponding with the ozone-transporting pipe;
        a fore end surface;
        a switch attached to the fore end surface for switching power supply or for adjusting bubble level;
    a bubble-outputting disc comprising
        multiple bubble-outputting holes; and
        a sleeve-head-connecting pipe inserted in one of the bubble-outputting hole, connected to the bubble-outputting disc and comprising
            a leading pipe connected to the bubble-outputting disc;
            an end; and
            radial holes formed on the end;
    a sink device comprising
        a surface;
    at least one sink formed on the surface of the sink device; and
    at least one gas-guiding disc respectively formed in the at least one sink, connected to the ozone generator that is connected to the control box for guiding an ozone gas generated by the ozone generator into the at least one sink to sterilize, deodorize and bleach an object to be cleansed and comprising
        multiple outlet holes through which the ozone gas generated by the ozone generator is guided into the sink;
    a utensil-holding device; and
    a vegetable basket.

* * * * *